United States Patent [19]

Weber et al.

[11] Patent Number: 4,531,243
[45] Date of Patent: Jul. 30, 1985

[54] ARTIFICIAL HIP JOINT SOCKET

[75] Inventors: Bernhard G. Weber, St. Gall; Otto Frey, Winterthur, both of Switzerland

[73] Assignee: Sulzer Brothers Limited, Winterthur, Switzerland

[21] Appl. No.: 533,960

[22] Filed: Sep. 20, 1983

[30] Foreign Application Priority Data

Oct. 5, 1982 [CH] Switzerland .................... 5839/82

[51] Int. Cl.³ ............................ A61F 1/04; A61F 5/04
[52] U.S. Cl. ...................................... 623/22; 623/66; 128/92 C
[58] Field of Search ................. 3/1.9, 1.91, 1.912, 3/1.911, 1.913; 128/92 C, 92 D, 92 CA, 92 B, 92 E

[56] References Cited

U.S. PATENT DOCUMENTS 3,903,549  9/1975  Deyerle ........................ 3/1.912
4,065,817  1/1978  Branemark et al. ........... 3/1.912

FOREIGN PATENT DOCUMENTS 0007393  2/1980  European Pat. Off. ......... 128/92 D
2318459  10/1974  Fed. Rep. of Germany ....... 3/1.912

Primary Examiner—Richard J. Apley
Assistant Examiner—David Isabella
Attorney, Agent, or Firm—Kenyon & Kenyon

[57] ABSTRACT

The hip joint socket is provided with a peripheral edge or flange in which a plurality of bores are formed. Each bore narrows conically from one side of the peripheral edge towards the free surface of the socket to provide outflow paths for excess bone cement which is displaced during implanting of the socket in a pelvis. The construction in the bores also permits the excess cement to harden into a rivet-like plug to increase the securement of the hip joint socket in the cement bed.

2 Claims, 3 Drawing Figures

ARTIFICIAL HIP JOINT SOCKET

This invention relates to an artificial hip joint socket. More particularly, this invention relates to an artificial hip joint socket for anchoring in a pelvis by means of a hardening bone cement.

Heretofore, various types of artificial hip joint sockets have been known for anchoring in a pelvis. For example, it has been known from French Pat. No. 7,315,945 and U.S. Pat. No. 3,943,576 to anchor hip joint sockets in a bone cement-free manner in a pelvis. In such cases, the sockets have been provided with bores which are distributed in the edge regions of the sockets in order to permit tissue to grow into the bores after implanting in order to firmly secure the socket in place.

It has also been known to implant hip joint sockets in a pelvis by means of a hardening bone cement. However, in these cases, difficulties often arise during the insertion of a socket due to the fact that the viscous bone cement, which is generally filled into the surgically produced recess in the pelvis bone in excess, cannot escape. Thus, the cement then flows over the lateral edge of the pressed-in socket, often moving into joint regions of the prosthesis where the cement may give rise to damage to the sliding surfaces of the artificial joint.

Accordingly, it is an object of the invention to provide a hip joint socket which can be implanted in a bone cement bed such that excess bone cement can be controlled in a guided manner.

It is another object of the invention to preclude excess bone cement from flowing into the joint region of a hip joint prosthesis during implantation of a socket in a cement bed.

It is another object of the invention to facilitate the implantation of a hip joint socket in a bone cement bed in a surgically prepared pelvis.

Briefly, the invention provides a hip joint socket for anchoring in a cement bed in a surgically prepared pelvis wherein the socket is provided with a recess of generally hemispherical shape, an outwardly directed edge or flange having a free surface about the recess and a plurality of bores in the flange. In accordance with the invention, each bore narrows from one side of the edge or flange in a direction towards the free surface. The narrowing of each bore, for example in a conical form, imparts a nozzle type effect on the "flow" of the viscous bone cement and opens up "beaten" paths for the excess cement. Thus, the excess cement issues from the edge of the joint socket in a plurality of worm-like streamers and is relatively easy to remove from the smooth, plane and relatively firm edge of the socket.

In order to improve the anchoring of the socket, each bore may narrow to a constriction located, for example in the median plane of the peripheral edge while widening from this plane toward the free surface. In this case, after hardening, the bone cement which fills the bores will act as a rivet union increasing the firm connection between the cement and socket.

These and other objects and advantages of the invention will become more apparent from the following detailed description taken in conjunction with the accompanying drawings wherein.

Figure 1:
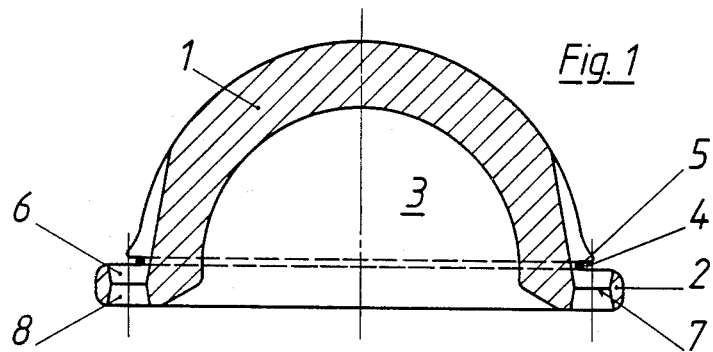
FIG. 1 illustrates a cross sectional view taken on line I—I of FIG. 2 of an artificial hip joint socket constructed in accordance with the invention.
Figure 2:
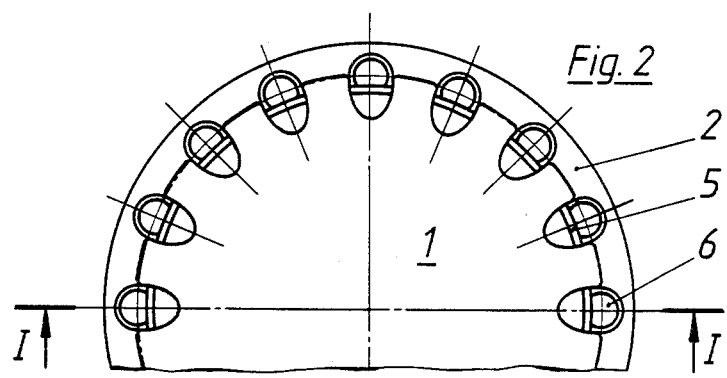
FIG. 2 illustrates a partial plan view of the socket of FIG. 1.

Referring to FIGS. 1 and 2, the artificial hip joint socket 1 is made of any suitable implant material, for example of a plastic such as polyethylene. As indicated in FIG. 1, the socket 1 presents an essentially hemispheric form which is closed off toward the equator by an outwardly directed peripheral edge or flange 2. Further, as shown, the socket 1 has a recess or shell of generally hemispherical shape for receiving a spherical head (not shown) of a femur prosthesis. In addition, a groove 4 is cut into the body of the socket 1 above the peripheral edge 2 in order to receive a metal wire ring 5 for use as an X-ray contrast element.

As shown in FIG. 1, the peripheral edge 2 defines a free surface about the recess 3 which presents a smooth plane appearance. In addition, a plurality of bores 6 are circumferentially spaced about and through the peripheral edge 2. Each bore 6 also narrows conically from one side of the peripheral edge 2 in a direction towards the free surface of the peripheral edge 2. As indicated in FIG. 1, each bore 6 narrows to a constriction 7 which is located in a median plane of the peripheral edge 2 and then widens conically towards the face surface in a counter-taper 8.

As indicated in FIG. 1, the bores 6 are disposed on parallel axes about the peripheral edge 2 and each is parallel to the central axis of the socket 1.

Figure 3:
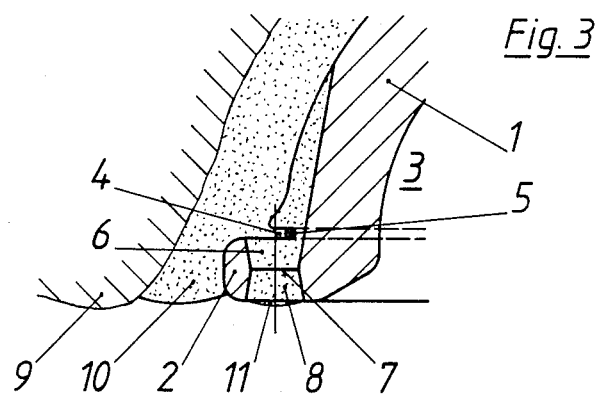
FIG. 3 illustrates a detail of a bore of the socket of FIG. 1 in a bone cement bed in a prepared pelvis in accordance with the invention.

Referring to FIG. 3, in order to implant the hip joint socket, a pelvis 9 is surgically prepared in known manner and a hardenable bone cement bed 10 is formed in the prepared pelvis 9. Next, the socket 9 is implanted in the cement bed 10 while excess bone cement is permitted to flow into and through the bores 6. The conical form of each bore 6 has a nozzle-like effect on the "flow" of the viscous bone cement and forms this excess material into a streamer which extends through the free surface of the peripheral edge 2. This excess material can then be readily removed by the surgeon since the peripheral edge 2 presents a smooth, plane and relatively firm surface. After hardening, the bone cement forms a rivet-like union or plug 11 so as to increase the firm connection between the bone cement bed 10 and the socket 1.

The invention thus provides a relatively simple means of implanting a hip joint socket in a hardenable bone cement bed while, at the same time, controlling the flow of excess bone cement. Further, the invention permits the otherwise excess bone cement to be utilized as a means for increasing the connection between the bone cement bed and the hip joint socket.

The invention further provides a hip joint socket wherein uncontrolled squeezing out of excess bone cement from a cement bed is precluded. As a result, bone cement is prevented from moving into positions between the sliding surfaces of a joint prothesis.

What is claimed is:

1. A method of implanting an artificial hip joint socket in a prepared pelvis, said method comprising the steps of forming a hardenable bone cement bed in the prepared pelvis, implanting a hip joint socket having an outwardly directed peripheral edge with a plurality of constricted bores each of which bores narrows from one side of the edge in a direction towards a free surface of the edge in the bone cement bed while permitting excess bone cement from the bed to flow into and through the bores, and removing the bone cement streaming from the bores at the free surface of the edge.

2. A method as set forth in claim 1 wherein each bore narrows to a constriction located in a plane of said edge and widens from said constriction to a free surface of said edge and the bone cement in each bore is permitted to harden in each bore to form a rivet-like union therein.

* * * * *

UNITED STATES PATENT AND TRADEMARK OFFICE
CERTIFICATE OF CORRECTION

PATENT NO. : 4,531,243

DATED : July 30, 1985

INVENTOR(S) : Bernhard G. Weber

It is certified that error appears in the above-identified patent and that said Letters Patent is hereby corrected as shown below:

Column 2, line 27 change "face" to -free-

Column 2, line 59 change "prothesis" to -prosthesis-

Signed and Sealed this

Twenty-eighth Day of January 1986

[SEAL]

Attest:

DONALD J. QUIGG

Attesting Officer     Commissioner of Patents and Trademarks